United States Patent [19]

Rosenberg et al.

[11] Patent Number: 4,538,618

[45] Date of Patent: Sep. 3, 1985

[54] FLUID FLOW DETECTOR PARTICULARLY USEFUL FOR MICROVASCULAR MONITORING

[76] Inventors: Lior Rosenberg, 13 Harduf St.; Jonathan Molcho, 29 Shikma St., both of Omer, Beer Sheva, Israel

[21] Appl. No.: 582,758

[22] Filed: Feb. 23, 1984

[30] Foreign Application Priority Data

Mar. 14, 1983 [IL] Israel ................................. 68115

[51] Int. Cl.³ .............................................. A61B 5/02
[52] U.S. Cl. .................................. 128/663; 128/691; 128/678
[58] Field of Search ............... 128/670, 678, 691, 694, 128/672, 677, 661, 662–663, 748; 73/204

[56] References Cited

U.S. PATENT DOCUMENTS

| 3,391,691 | 7/1968 | Young | 128/678 |
| 3,920,004 | 11/1975 | Nakayama | 128/691 X |
| 4,079,730 | 3/1978 | Wikswo, Jr. et al. | 128/691 X |
| 4,127,114 | 11/1978 | Bretscher | 128/663 |
| 4,249,540 | 2/1981 | Koyama et al. | 128/691 X |

FOREIGN PATENT DOCUMENTS 2823392 12/1979 Fed. Rep. of Germany ...... 128/691

OTHER PUBLICATIONS

Krosner et al.; "Fluid Path In–Line Detection of Flow, Press, Conduct, and/or Opacity"; *IBM Techn. Discl. Bull.*, vol. 17, No. 5, 10-1974, pp. 1282-1283.

*Primary Examiner*—Lee S. Cohen
*Assistant Examiner*—Angela D. Sykes
*Attorney, Agent, or Firm*—Benjamin J. Barish

[57] ABSTRACT

A fluid flow detector for the non-invasive detection of fluid flow particularly useful for microvascular monitoring comprises a head adapted to be placed against the object through which the fluid flows, a Doppler fluid flow sensor carried by the head, and a pressure transducer carried by the head for measuring the pressure applied thereby against the object.

11 Claims, 5 Drawing Figures

U.S. Patent  Sep. 3, 1985  4,538,618
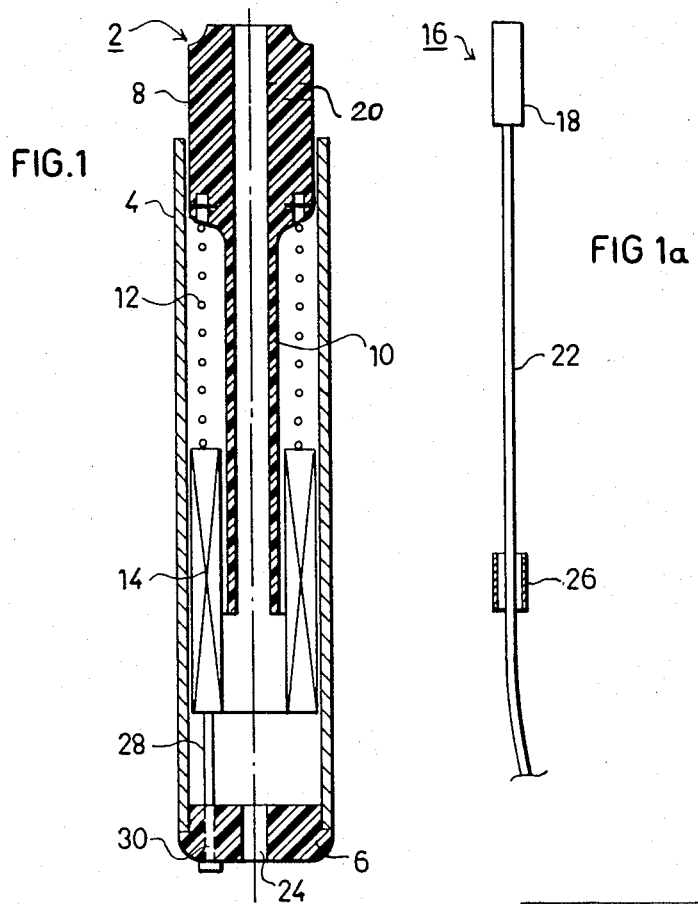
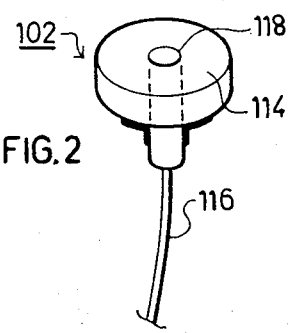
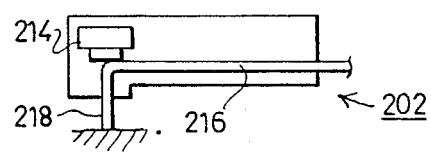
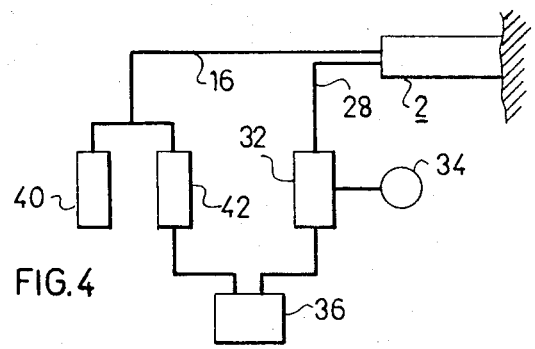

4,538,618

FLUID FLOW DETECTOR PARTICULARLY USEFUL FOR MICROVASCULAR MONITORING

BACKGROUND OF THE INVENTION

The present invention relates to fluid flow detectors for detecting the flow of a fluid through an object. The invention is particularly useful for microvascular monitoring, i.e. for monitoring minute variations in the blood flowthrough skin or other tissue and is therefore described below with respect to this application.

Detection of minute variations in blood flow at the capillary level is essential for the diagnosis of tissue viability in certain conditions, such as in burns, flaps, tissue trauma and ischemia, and central and perpheral circulation disorders. An early and accurate diagnosis of tissue viability is necessary for both optimal treatment and optimal prognosis. Because of the extremely small size of the capillary, and the very slow blood current, the presently used methods have mostly been indirect methods, measuring the effects of blood flow rather than directly measuring blood flow, moreover, they are not very precise and usually provide, at best, merely an estimation of the quantity of blood that arrives from the center to the measured site.

One of the recently-proposed methods for microvascular monitoring is based on the Doppler effect, wherein a high-frequency wave, preferably of laser light but also conceivably of ultrasound, is transmitted via a waveguide, or directly to the site and reflected back to a receiver, the frequency shift between the transmitted and reflected waves being an indication of the blood flow at the examined site. Such detectors show promise for the non-invasive and real-time detection of blood flow, but insofar as we are aware, they have not yet been developed to the point of practical use.

SUMMARY OF THE INVENTION

An object of the present invention is to provide a detector for detecting fluid flow through an object, which detector is particularly useful for microvascular monitoring. Another object of the invention is to provide such a microvascular monitor based on the Doppler effect, but providing a number of important advantages over the detectors heretofore proposed as will be described more particularly below.

According to a broad aspect of the present invention, there is provided a fluid flow detector for the non-invasive detection of the flow of a fluid through an object, which detector is particularly useful for microvascular monitoring, comprising a head adapted to be placed against the object; fluid-flow sensing means carried by the head for sensing the flow of fluid through the object when the head is applied against it; and a pressure transducer carried by the head for measuring the pressure applied thereby against the object.

A fluid flow detector constructed in accordance with the foregoing features provides a number of important advantages, particularly when used for microvascular monitoring. Thus, by providing an indication of the pressure applied by the head to the subject's tissue at the time the blood flow through the tissue is measured, important information is made available as to the nature of the measured blood flow, i.e., whether flowing through arteries, veins, shunt or capillaries. Further, pressure reference points for "zero" blood flow and for maximum blood flow may be provided, thereby enabling a better determination of the quality and total quantity of blood flow. Still further, the novel arrangement permits the measurement of blood flow to be related to predetermined pressures of application of the head, thereby providing better reference points for interpreting blood flow measurements.

In the preferred embodiment of the invention, as described below, the fluid-flow sensing means monitors the fluid flow by the Doppler effect. For this purpose the fluid flow sensing means comprises a waveguide carried by the head and adapted to be coupled at one end to a transmitter and receiver of high frequency waves so as to measure the fluid flow by the Doppler effect. Preferably, the waveguide is of the optical fibre type to guide laser light from the transmitter to the object and back from the object to the receiver. Conceivably, the ultrasonic wave could be guided to and from the measurement site by a waveguide, or could be generated and detected right at the measurement site.

Three embodiments of the invention are described below. In one described embodiment, the waveguide is carried by the detector head so as to be displaced in accordance with the pressure applied by the head to the object, the pressure transducer including means to measure the amount of this displacement and thereby to produce a measurement of the pressure applied. In a second described embodiment; the waveguide is fixed within the head, and the pressure transducer, which may for example be of the semiconductor type, is disposed so as to directly sense the pressure applied by the head against the object. In a third described embodiment, the pressure transducer directly senses the pressure applied by the waveguide to the object.

Further features and advantages of the invention will be apparent from the description below.

The invention as herein described, by way of example only, with reference to the accompanying drawings, wherein:

BRIEF DESCRIPTION OF THE DRAWINGS

FIGS. 1 and 1a together illustrate one form of detector head constructed in accordance with the invention, FIG. 1 illustrating the main parts of the head, and FIG. 1a illustrating the waveguide receivable within the head for coupling same to a high frequency transmitter and receiver to detect fluid flow by the Doppler effect;

FIG. 2 is a three-dimensional view illustrating another fluid-flow-pressure detector in accordance with the invention;

FIG. 3 illustrates a third detector head constructed in accordance with the invention; and FIG. 4 is a block diagram illustrating an electronic set-up which may be used with the head of any one of FIGS. 1–3 for microvascular monitoring of blood flow through skin or other tissue of a subject's body.

DESCRIPTION OF PREFERRED EMBODIMENTS

The fluid flow detector illustrated in FIGS. 1 and 1a, and therein generally designated 2, is a microvascular monitor head for monitoring minute variations in the blood flow through skin or other tissue. It includes a cylindrical housing 4 closed at one end by a plug 6, and at the opposite end, a plunger 8 formed with a hollow stem 10 displaceable within the housing against the action of spring 12. The latter spring is disposed between the inner end of plunger 8 and an electrical coil 14 fixed within the housing, with the hollow stem 10 of the plunger disposed within the coil.

The head 2 of FIG. 1 further includes an optical fiber illustrated in FIG. 1a and therein generally designated 16. Optical fiber 16 includes an enlarged end 18 to be secured within plunger 8 by means of a fastener 20 passing through the plunger and engaging the head 18, such that the outer face of the enlarged end 18 is flush with the outer face of the plunger. The main portion of optical fiber 16 is in the form of a long tail 22 passing through the hollow stem 10 of a plunger 8 and out through a bore 24 formed through plug 6 at the opposite end of the housing. As shown in FIG. 1a, an iron core 26 is secured to the portion of the optic fiber tail 22 disposed within the electrical coil 14 fixed in housing 4 so that the core is displaceable within the coil according to the displacement of the plunger 18 within the housing. By fixing the core 26 to the optical fiber tail 22, the location of the core with respect to the coil 14 may be conveniently adjusted, i.e., for zeroing purposes. It will be appreciated, however, that core 26 could also be fixed directly to stem 10 of the plunger 8.

The head illustrated in FIGS. 1 and 1a is for use with a source of a laser light beam, in which case the optical fiber 16 serves as a waveguide for directing the laser beam to the object and for returning the reflected laser beam back to a receiver in order to sense the blood flow by the Doppler effect, namely by the frequency shift between the transmitted and reflected waves. During this measurement, coil 14 fixed within housing 4 and core 26 displaceable with plunger 8, serves as a pressure transducer for measuring the pressure applied by the head 2 to the subject. Thus, this pressure is converted to a displacement of the plunger, and thereby of core 26, which displacement is measured by coil 14. The electrical measurement of this displacement is outputted from coil 14 via its input-output leads 28 passing through another bore 30 in the end plug 6 of the detector housing 4.

The microvascular monitor head 2 illustrated in FIGS. 1 and 1a may be used in the following manner, references also being made to the system block diagram illustrated in FIG. 4.

First, the optical fiber 16 is inserted through housing 4 and its plunger 8 flush with the outer face of the plunger. It is fixed in this position by fastener 20 passing through the plunger and engaging the outer surface of fiber end 18. This is done when the end plug 6 has been removed from the housing 4, so that the core 26 may be moved to its "zero" position with respect to the electrical coil 14 and retained as by friction, in that position. Plug 6 is then secured to the end of the housing with the tail 22 of the optical fiber passing through bore 24 of the plug, and with the coil input-output leads passing through bore 30 of the plug.

In use, the head 2 is gripped by the operator and is manipulated so as to apply pressure to the skin or other tissue being monitored. This pressure will cause plunger 8 to be displaced against the action of spring 12, so that the core 26 will in turn be displaced with respect to the coil 14 a distance corresponding to the pressure of application of the head against the subject's tissue. Coil 14 will therefore output an electrical signal via its leads 28 corresponding to the pressure of application of the head to the subject's skin. At the same time, the laser 40 (FIG. 4) is energized so as to transmit a laser beam through one branch of the optical fiber 16, which beam is reflected back through another branch of the same optical fiber to the receiver unit 42, for measuring the blood flow through the tissue according to the Doppler effect.

As shown in FIG. 4, the electrical signal from leads 28 is applied to a pressure signal processor 32 which computes the pressure and outputs same to a pressure indicator 34, so that the operator can continuously see the magnitude of the pressure applied to the subject's skin. If desired, this pressure can also be fed to the recorder 36 provided for recording the blood-flow pressure information measured by the head 2 according to the Doppler effect.

As further shown in FIG. 4, laser 40 is coupled to the end of the optical fiber 16 which transmits the laser beam via one branch thereof to the subject, and also transmits via another branch thereof, the laser light reflected from the subject. As known, the laser light imprinting the subject's tissue or skin is scattered by the moving red blood cells in the skin, and also by stationary tissue. The light scattered by the moving red blood cells undergoes a frequency shift according to the Doppler effect. The scattered light thus transmitted back through the optical fiber 16 is fed to an optical detector and processor 42 which produces an output Doppler signal having a DC component proportional to the amount of light scattered by the skin, and an AC component resulting from heterodyning of the frequency-shifted and unshifted light fields. This Doppler signal is processed in processor 42 to produce an output electrical signal proportional to the skin perfusion.

It will be appreciated that the Doppler signal corresponds to tissue blood flow, which differs between healthy tissue and affected tissue; thus, the Doppler signal provides an indication of the perfusion impairment inflicted on the capillary bed.

The monitoring of the blood flow by this Doppler effect is well know, and therefore further details of the construction and operation of such a monitor are not deemed necessary. The novelty here, however, is the provision of the pressure transducer for measuring the pressure of application of the head to the skin, which provides pressure information that can be of great value in the use of the head particularly when used for microvascular monitoring.

Thus, providing a reading of the pressure applied by the heat to the subject's skin at the time of monitoring the blood flow enables the user to better determine the different components of the total blood flow measured. For example, the head may first be applied with increasing pressure against the subject's skin or other tissue until all blood flow is stopped, and then may be slowly released, whereupon the first blood flow sensed will be that flowing through the arteries of the examined zone, since they have the highest blood pressure. As the pressure of application of the head is further reduced, a greater portion of the measured blood flow will be attributable to the other blood vessels, namely the veins, shunts and capillaries.

In addition, the flow-pressure relationship provides a better index of comparison for any particular measurement. Thus, by comparing the differences of measured blood flow at a predetermined pressure of application, more useful results can be obtained.

Still further, the illustrated head may be used to provide a reference point for "zero" blood flow, and also for maximum blood flow, thereby enabling a better determination to be made of the total quantity of blood flow at the maximum, minimum or any intermediate pressure therebetween.

FIG. 2 illustrates another microvascular monitor head constructed in accordance with the invention. In this case, the head, generally designated 102, also includes a pressure transducer, but here the pressure transducer, generally designated 114, is not of the displaceable type as in FIGS. 1 and 1a, but rather is of the non-displaceable type, such as a semiconductor or piezoelectric crystal, which directly senses the pressure applied against the subject's tissue. The microvascular monitor head 102, illustrated in FIG. 2 is otherwise the same as in FIGS. 1 and 1a, including an optical fiber, generally designated 116, serving as a waveguide for transmitting the laser beam from one end of the optical fiber to the opposite end 118, and also for transmitting back to the measuring circuit, such as illustrated in FIG. 4, the laser light reflected from the subject's skin determining blood flow therethrough in accordance with the Doppler effect. As in FIG.1, the outer face of the enlarged end 118 of the optical fiber 116 is also substantially flush with the outer face of the head 102, in this case the outer face of the pizoelectric pressure transducer 114.

FIG. 3 illustrates a further variation, wherein the microvascular monitor head, generally designated 202, also includes a pressure transducer 214, but in this case the pressure transducer does not bear directly against the subject's tissue, but rather bears against the optical fiber 216 serving as the wave guide or the transmitted and reflected laser light which waveguide bears directly against the subject's tissue. Thus, head 218 of the optical fiber is not flush with the outer face of the head, but rather projects through the other face of the head so as to be brought into direct contact with the subject's tissue. Optical fiber 216 is mounted within the head 202 for movement within the head; thus, the pressure applied to the end of the waveguide when the head is pressed against the subject's tissue is transmitted to the pressure transducer 214. The head of FIG. 3 may otherwise be constructed and operated as described above with respect to the head of FIGS. 1 and 1a.

While the microvascular monitor heads illustrated in the drawings have been described as using laser light beams to measure blood flow by the Doppler effect, it will be appreciated that these heads could use other arrangements for measuring blood flow, for example ultrasonic waves, in which case the optical fiber (e.g. 16) serving as the waveguide for the laser light beam would be replaced by an ultrasonic device. In addition, the microvascular monitor head could include means for collecting other data commonly included in such heads, such as temperature, partial pressure of oxygen ($PO_2$), partial pressure of carbon dioxide ($PCO_2$), oxyhemoglobin, and reflectance or transmittance. While the invention has been described with respect to monitoring blood flow, it will be appreciated that the invention could advantageously be used for non-invasive monitoring of fluid flow through other objects, such as through non-rigid pipes or other fluid conduits or networks.

Further variations, modifications and applications of the invention will be apparent.

What is claimed is:

1. A fluid flow detector for the non-invasive detection of the flow of a fluid through an object, which detector is particularly useful for microvascular monitoring, comprising:
    a head adapted to be placed against the object;
    fluid-flow sensing means carried by said head for sensing the flow of fluid through the object when the head is applied against it; and
    pressure transducer means carried by said head for measuring the pressure applied thereby against the object.

2. The detector according to claim 1, wherein said fluid-flow sensing means senses fluid-flow by the Doppler effect.

3. The detector according to claim 2, wherein said fluid-flow sensing means comprises a device carried by the head adapted to be coupled at one end to a transmitter and receiver of high frequency waves so as to measure the fluid flow by the Doppler effect.

4. The detector according to claim 3, wherein said device includes an optical fiber for guiding laser light from the transmitter to the object, and from the object to the receiver.

5. The detector according to claim 3, wherein said device is an ultrasonic waveguide for guiding ultrasonic sound from the transmitter to the object, and from the object to the receiver.

6. The detector according to claim 3, wherein said device is carried by the head so as to be displaced within the head in accordance with the pressure applied thereby to the object, said pressure transducer means including means for measuring the magnitude of said displacement and thereby producing a measurement of said pressure.

7. The detector according to claim 6, wherein said device is carried by a plunger displaceable within the head against the action of a spring, said pressure transducer means including an iron core displaceable with said device, and an electrical coil fixed within the head to sense the magnitude of displacement of the core.

8. The detector according to claim 3, wherein said device is fixed within said head, and said pressure transducer means is of the non-displaceable type.

9. The detector according to claim 8, wherein said pressure transducer means is disposed so as to directly sense the pressure applied by the head against the object.

10. The detector according to claim 8, wherein said pressure transducer means is disposed so as to directly sense the pressure applied by said device against the object.

11. The detector according to claim 8, wherein said pressure transducer means is of the piezoelectric crystal type.

* * * * *